United States Patent
Dondeyne et al.

(10) Patent No.: US 10,537,502 B2
(45) Date of Patent: Jan. 21, 2020

(54) TWO-PHASE MAKE-UP REMOVAL COMPOSITION

(71) Applicant: CHANEL PARFUMS BEAUTE, Neuilly sur Seine (FR)

(72) Inventors: Corinne Dondeyne, Rueil Malmaison (FR); Thibault Schirmann, Kremlin Bicetre (FR); Véronique Trouillet, Saint Pierre les Nemours (FR)

(73) Assignee: CHANEL PARFUMS BEAUTE, Neuilly sur Seine (FR)

( * ) Notice: Subject to any disclaimer, the term of this patent is extended or adjusted under 35 U.S.C. 154(b) by 0 days.

(21) Appl. No.: 16/086,839

(22) PCT Filed: Mar. 31, 2017

(86) PCT No.: PCT/FR2017/050741
§ 371 (c)(1),
(2) Date: Sep. 20, 2018

(87) PCT Pub. No.: WO2017/191382
PCT Pub. Date: Nov. 9, 2017

(65) Prior Publication Data
US 2019/0083369 A1 Mar. 21, 2019

(30) Foreign Application Priority Data

Apr. 1, 2016 (FR) .................................. 16 52853

(51) Int. Cl.
| | | |
|---|---|---|
| C11D 3/37 | (2006.01) | |
| A61K 8/03 | (2006.01) | |
| A61Q 1/14 | (2006.01) | |
| A61K 8/55 | (2006.01) | |
| A61K 8/73 | (2006.01) | |
| A61K 8/86 | (2006.01) | |
| A61Q 19/10 | (2006.01) | |
| A61K 8/92 | (2006.01) | |
| A61K 8/90 | (2006.01) | |
| A61K 8/368 | (2006.01) | |
| A61K 8/39 | (2006.01) | |
| A61K 8/60 | (2006.01) | |

(52) U.S. Cl.
CPC ................ *A61K 8/03* (2013.01); *A61K 8/368* (2013.01); *A61K 8/39* (2013.01); *A61K 8/553* (2013.01); *A61K 8/60* (2013.01); *A61K 8/73* (2013.01); *A61K 8/86* (2013.01); *A61K 8/90* (2013.01); *A61K 8/922* (2013.01); *A61Q 1/14* (2013.01); *A61Q 19/10* (2013.01)

(58) Field of Classification Search
CPC . A61K 8/553; A61K 8/60; A61K 8/86; A61K 8/90; A61K 8/04; A61K 8/03; A61K 8/368; A61K 8/39
See application file for complete search history.

(56) References Cited

U.S. PATENT DOCUMENTS

| | | | | |
|---|---|---|---|---|
| 2009/0196894 A1* | 8/2009 | Ehlis | ...................... | A61K 8/044 424/401 |
| 2012/0093896 A1* | 4/2012 | Mongiat | .................. | A61K 8/04 424/401 |

FOREIGN PATENT DOCUMENTS

| | | |
|---|---|---|
| CN | 103505381 | 1/2014 |
| EP | 1 514 534 | 3/2005 |
| EP | 1 894 994 | 3/2008 |
| JP | 2006-306842 | 11/2006 |
| JP | 2011-213682 | 10/2011 |
| JP | 2013-075867 | 4/2013 |
| WO | WO 2015/091380 | 6/2015 |

OTHER PUBLICATIONS

International Search Report, PCT/FR2017/050741, dated Jun. 12, 2017.
Database WPI Week 201420, Thomson Scientific, London, GB; AN 2014-E84186 XP002759283, -& CN 103 505 381 A (Guangzhou Huanya Cosmetics SCI & Technol) Jan. 15, 2014 (Jan. 15, 2014).
Database WPI Week 201330, Thomson Scientific, London, GB; AN 2013-G14012 XP002759284, -& JP 2013 075867 A (KAO Corp) Apr. 25, 2013 (Apr. 25, 2013) abstract.
Database WPI Week 201173, Thomson Scientific, London, GB; AN 2011-N36238 XP002759285, -& JP 2011 213682 A (Narisu Keshohin KK) Oct. 27, 2011 (Oct. 27, 2011) abstract.
Database WPI Week 200702, Thomson Scientific, London, GB; AN 2007-012383 XP002759286, -& JP 2006 306842 A (Kose KK) Nov. 9, 2006 (Nov. 9, 2006) abstract.

* cited by examiner

*Primary Examiner* — John R Hardee
(74) *Attorney, Agent, or Firm* — Young & Thompson

(57) ABSTRACT

Disclosed is a cosmetic composition composed of an aqueous phase and a separate water-in-oil or oil-in-water emulsion including at least 20% by weight of an oil phase in relation to the total weight of the composition; and the composition including an emulsifying system containing an inulin derivative, a lysophospholipid, a poloxamer, a polypropylene glycol buteth, and a derivative of hydrogenated castor oil.

20 Claims, No Drawings

TWO-PHASE MAKE-UP REMOVAL COMPOSITION

The purpose of this invention is a cosmetic composition, particularly for topical application, composed of two separate phases, an aqueous phase and a water-in-oil (W/O) or oil-in-water (O/W) phase, the composition comprising a specific emulsifying system, and said W/O emulsion comprising at least 20% by weight of an oil phase in relation to the total weight of the composition. Another purpose of this invention is the use of said composition in the cosmetic or dermatological field, particularly for make-up removal, cleaning and/or care of the skin, eyes and/or appendages.

Cosmetic compositions composed of two separate phases, particularly an aqueous phase and a phase comprising oily compounds, said phases being separate from each other and not emulsified in each other at rest, are usually designated by the term "two-phase" compositions. They are different from emulsions in that, at rest, the two phases are separate, instead of being an emulsion of one in the other. The use of these two-phase compositions requires prior shaking to form an emulsion, that must have sufficient quality and stability to enable homogeneous application of the two phases on the skin or keratinous material on which it is applied. At rest, said phases must separate quickly and return to their initial state, this phenomenon being referred to as "phase separation".

Fast phase separation (or demixing) of the two phases after their use is one of the required qualities of two-phase compositions. Obtaining fast phase separation is desirable for various reasons, particularly because poor separation between the two phases is perceived as being inaesthetic by users. But it is difficult to find phase separation agents that can give good phase separation without the formation of foam in the oily phase of the two-phase mixture when shaking. This formation of foam is unacceptable for the user.

Furthermore, with classical two-phase compositions, an emulsion is not necessarily formed after shaking the composition, which leads to unsatisfactory make-up removal, and leaves a greasy residue on the skin or the keratinous material.

Therefore there is still a need for a two-phase composition composed of two separate immiscible phases that, after shaking and extemporaneous and transient formation of emulsion, separates quickly into two phases without the formation of foam. After preliminary shaking, such a two-phase composition must also form a transient emulsion that enables application of the composition and efficient make-up removal, without the formation of a greasy residue on the skin or keratinous material.

Surprisingly, the applicant has developed a two-phase formulation with the required qualities, in other words that separates quickly into two clear phases after use, without the formation of foam in the oily phase during shaking. This formulation forms a transient emulsion after shaking and enables efficient make-up removal, without leaving a greasy residue.

The purpose of this invention is thus a cosmetic composition composed of an aqueous phase and a separate water-in-oil or oil-in-water phase, the composition comprising an emulsifying system containing an inulin derivative, a lysophospholipid, a poloxamer, a polypropylene glycol buteth and a derivative of hydrogenated castor oil, and the water-in-oil or oil-in-water emulsion comprising at least 20% by weight of an oil phase in relation to the total weight of the composition.

The cosmetic composition according to the invention is composed of two separate phases, an aqueous phase and a water-in-oil or oil-in-water phase, and emulsifies easily by shaking and phase separation occurs easily after shaking is stopped.

The composition according to the invention is preferably intended for topical application.

The composition according to the invention comprises a separate water-in-oil or oil-in-water emulsion and an aqueous phase. These two phases are separate, in other words they can be seen to be one above the other when at rest. They are also transparent at rest. Each of the phases may be coloured or colourless. After shaking, such a composition forms a transient oil-in-water phase, ready for use.

The composition according to the invention comprises an oily phase that is present in the water-in-oil or the oil-in-water emulsion. This oily phase is present with a quantity equal to at least 20% by weight of the total weight of the composition. The composition according to the invention also comprises a global aqueous phase corresponding to the entire aqueous phase present in the composition (namely the aqueous phase itself, and the aqueous phase of the water-in-oil or oil-in-water emulsion). Preferably, the global aqueous phase:oily phase ratio is between 40:60 and 80:20. Within these ratios, tests carried out show stable compositions, particularly at D+2 at ambient temperature.

The water-in-oil or oil-in-water phase emulsion phase of the composition according to the invention comprises at least 20% by weight of an oil phase in relation to the total weight of the composition. Preferably, the oily phase is present with a content of between 20% and 40%, and preferably between 25% and 35% by weight of the total weight of the composition, and preferably about 30% by weight.

The composition according to the invention also comprises an emulsifying system comprising an inulin derivative, a lysophospholipid, a poloxamer, a polypropylene glycol buteth and a derivative of hydrogenated castor oil.

This specific emulsifying system is well tolerated, enables efficient make-up removal, increases moisturisation, prevents the formation of foam and stabilises the emulsion obtained. It also makes it possible to prepare the composition according to the invention cold.

In particular, the poloxamer is particularly surprising in that it prevents the formation of foam, which is not the case for other emulsifiers, as will be demonstrated later in the comparative examples. Furthermore, the presence of polypropylene glycol buteth and a derivative of hydrogenated castor oil stabilises the water-in-oil emulsion and results in good phase separation between this emulsion and the aqueous phase.

Preferably, the emulsifying system is present in the composition according to the invention with a content of between 2% and 10%, and preferably between 3% and 7% by weight of the total weight of the composition.

Preferably, the derivative of inulin is an inulin carbamoyl with an alkyl (preferably lauryl) isocyanate, and preferably said derivative is inulin lauryl carbamate. Inulin lauryl carbamate satisfies the following formula (I):

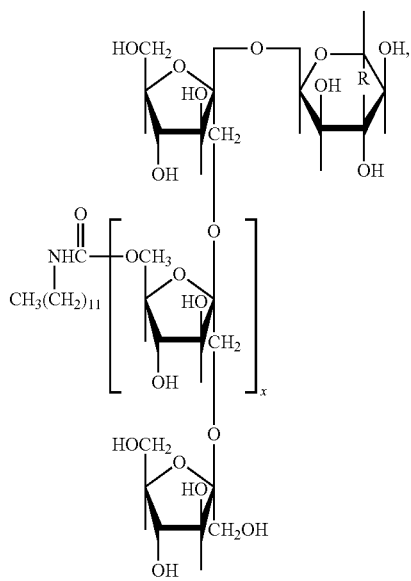

(I)

in which x is an integer between 2 and 65, preferably between 20 and 65, and R is a hydroxymethyl group. Inulin lauryl carbamate with a content of 25% by weight is marketed particularly in the form of glycerine with 75% by weight by Gova Group under the trade name Inutec SL1®.

The polypropylene glycol buteth is a polyoxypropylene, polyoxyethylene ether of butyl alcohol satisfying the following formula (II):

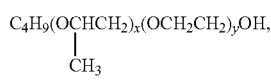

(II)

in which x and y are integers that may be identical or different, between 1 and 50, and preferably between 10 and 35. Preferably, the polypropylene glycol buteth is chosen from among PPG-12-buteth-16 (formula (II) in which x=12 and y=16), PPG-9-buteth-12 (formula (II) in which x=9 and y=12), PPG-26-buteth-26 (formula (II) in which x=26 and y=26) and PPG-28-buteth-35 (formula (II) in which x=28 and y=35).

Preferably, the derivative of hydrogenated castor oil is an oxyethylenated hydrogenated castor oil, preferably comprising between 20 and 50 moles of ethylene oxide More preferably, said derivative is PEG-30 hydrogenated castor oil or PEG-40 hydrogenated castor oil.

Preferably, a mixture of PPG-26-buteth-26 and PEG-40 hydrogenated castor oil will be used. More preferably, the mixture of PPG-26-buteth-26 at between 60% and 65% by weight, and PEG-40 hydrogenated castor oil at between 35% and 40% by weight is used, preferably marketed by Sensient Cosmetic Technologies under the trade name Solubilisant LRI®.

The poloxamers are non-ionic copolymers with three blocks, typically having a hydrophobic central block of polypropylene glycol, and two external hydrophilic blocks of polyethylene glycol. They satisfy the following formula (III):

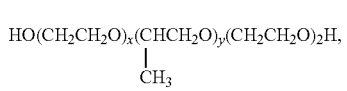

(II)

in which x and y are integers that may be identical or different, between 1 and 50, and preferably between 10 and 35.

The poloxamers are marketed particularly under the names Pluronic (BASF) Kolliphor (BASF) and Synperonic (Croda International). The poloxamer is preferably poloxamer 184 (formula (III) in which x=z=13, y=30), like that marketed by BASF under the name Pluracare® L64 or that marketed by Croda under the name Synperonic PE L64.

The lysophospholipid designates a phospholipid that has lost one or several acyl groups, particularly by hydrolysis. The lysophospholipid used in the composition according to the invention is lysophosphatidylcholine, with the following formula:

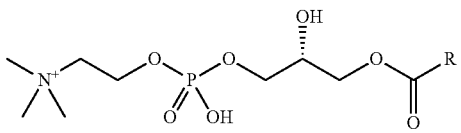

in which R is a fatty acid chain, in particular comprising 10 to 25, and preferably 15 to 20, carbon atoms.

The lysophospholipid used in the composition according to the invention is preferably derived from soybean seeds. Preferably, its INCI name is glycine soybean seed extract. Preferably, a mixture of 80% by weight of glycerine and 20% by weight of glycine soybean seed extract marketed by Kemin under the trade name Lysofix Liquid® will be used.

Preferably, the quantity of poloxamer is equal to the quantity of lysophospholipid. Preferably, the inulin derivative:lysophospholipid:poloxamer-polypropylene glycol buteth:oxygenated castor oil derivative ratio of the emulsifying system is about (0.30 to 0.40):(0.90 to 1.10):(0.90 to 1.10):(0.80 to 0.90): (0.50 to 0.65), and preferably about 0.36:1:1:0.86:0.57.

Preferably, the composition also comprises gluconolactone and/or sodium benzoate. Such compounds are efficient preservatives, and are acceptable in cosmetics. Preferably, the composition comprises a mixture of gluconolactone, sodium benzoate and calcium gluconate. Such a mixture is marketed particularly by Lonza under the name Geogard Ultra®. Preferably, gluconolactone and/or sodium benzoate, and optionally calcium gluconate, are present in a quantity varying from 0.5% to 3% by weight.

The oily phase of the composition according to the invention may be composed of several oils, including mineral, vegetable or synthetic oils.

According to one preferred embodiment of the invention, the oily phase comprises one or several oils chosen from among hydrocarbon oils with mineral or synthetic origin and silicone oils. More particularly, the oily phase advantageously contains one or several volatile oils chosen from among volatile hydrocarbon oils with mineral or synthetic origin and volatile silicone oils.

A hydrocarbon oil is an oil formed essentially, or even composed of, carbon and hydrogen atoms, and possibly oxygen, nitrogen atoms and not containing any silicon or fluorine atoms; it can contain, ester, ether, amine or amide groups.

Among volalite hydrocarbon oils with mineral or synthetic origin, mention may be made of iso-alkanes (also called isoparaffins) in $C_8$-$C_{16}$, such as isododecane, isodecane, isohexadecane, for example such as iso-alkanes sold under the trade name Isopar by the Exxon Chemical company or oils sold under the trade name Permethyl by the Presperse company, and mixtures thereof.

Among non-volatile hydrocarbon oils with mineral or synthetic origin, mention may be made of petrolatum oil, hydrogenated polyisobutene such as Parleam® oil, and mixtures thereof.

Silicone oil refers to an oil containing at least one silicon atom and particularly containing Si—O groups. Silicone oil may be chosen from among non-volatile silicone oils, volatile silicon oils and mixtures thereof.

Examples of volatile silicone oils include particularly cyclopolydimethylsiloxanes (INCI name cyclomethicone), such as cyclopentasiloxane, cyclohexasiloxane, octamethyl-cyclotetrasiloxane, decamethylcyclopentasiloxane, dodecamethylcyclohexasiloxane; linear silicones such as heptamethylhexyltrisiloxane, heptamethyloctyl-trisiloxane, hexamethyl-disiloxane, octamethyltrisiloxane, decamethyltetrasiloxane, dodecamethyl pentasiloxane, and mixtures thereof.

Among non-volatile silicone oils, mention may be made of polydimethylsiloxanes (PDMS), phenylated polymethylsiloxanes such as phenyltrimethicones, phenyldimethicones, phenyltrimethylsiloxydiphenylsiloxanes, diphenyl-dimethicones, diphenylmethyldiphenyl trisiloxanes, 2-phenylethyltrimethyl-siloxysilicates, and polymethylphenylsiloxanes; polysiloxanes modified by fatty acids, fatty alcohols or polyoxyalkylenes, and mixtures thereof.

Among vegetable or synthetic oils that can be used in the composition according to the invention, mention may be made for example of:
  hydrocarbon oils of vegetable origin, such as liquid triglycerides of fatty acids containing 4 to 10 carbon atoms such as triglycerides of heptanoic or octanoic acids, or also for example sunflower, maize, soybean, pumpkin, grapeseed, sesame, hazelnut, apricot stone, macadamia, arara, coriander, castor, avocado oils, triglycerides of caprylic/capric acids like those sold by the Stearineries Dubois company or those sold under the trade names Miglyol 810, 812N and 818 by the Dynamit Nobel company, jojoba oil or shea butter oil;
  synthetic esters and ethers, particularly of fatty acids, such as oils with formulas $R^1COOR^2$ and $R^1 OR^2$ in which $R^1$ represents the remainder of a fatty acid comprising 8 to 29 carbon atoms, and $R^2$ represents a branched or unbranched hydrocarbon chain, containing 3 to 30 carbon atoms, for example such as Purcellin oil, isononyl isononanoate, isopropyl myristate, isopropyl palmitate, ethyl-2-hexyl palmitate, octyl-2-dodecyl stearate, octyl-2-dodecyl erucate, isostearyl isostearate; hydroxylated esters such as isostearyl lactate, octylhydroxystearate, octyldodecyl hydroxystearate, diisostearylmalate, triisocetyl citrate, heptanoates, octanoates, decanoates of fatty alcohols; polyol esters such as propylene glycol dioctanoate, neopentylglycol diheptanoate and diethyleneglycol diisononanoate; pentaerythritol esters such as pentaerythrityl tetraisostearate; and mixtures of coco alcohol esters with caprylic and capric acid (coco-caprylate/caprate) and alkanes of coco, such as the mixture with INCI name coconut alkanes (and) coco-caprylate/caprate, sold under the name Vegelight 1214LC® by Grant Industries.

Preferably, the oily phase comprises at least one volatile oil, preferably isohexadecane. Preferably, the oily phase comprises at least triglycerides of caprylic/capric acids and/or mixtures of coco alcohol esters with caprylic and capric acid (coco-caprylate/caprate) and coco alkanes.

Preferably, the composition also comprises at least one anti-foaming agent, preferably simethicone. Such an agent is marketed particularly under the name Xiameter ACP-1500 Antifoam Compound®.

The composition may also comprise a salt, for example such as sodium chloride, that has no effect on phase separation but is used as an additive in an eye make-up removal composition so that the osmotic pressure of the composition is similar to that of tears. The quantity of salt(s)may for example vary from 0.01 to 5% by weight, and preferably from 0.01 to 3% by weight, and even better from 0.05 to 2% by weight of the total weight of the composition.

The aqueous phase of the composition according to the invention comprises water and any water soluble or water dispersible additive. The water used may be sterile demineralised water and/or floral water such as rose water, blueberry water, chamomile water or linden water, and/or a natural thermal or mineral water for example such as Vittel water, Vichy basin water, Uriage water, Roche Posay water, Bourboule water, Enghien-les-Bains water, Saint Gervais-les-Bains water, Néris-les-Bains water, Allevar-les-Bains water, Digne water, Maiziéres water, Neyrac-les-Bains water, Lons-le-Saunier water, Eaux Bonnes water, Rochefort water, Saint Christau water, Fumades and Tercis-les-bains water, Avéne water.

Among hydrosoluble additives, mention may be made particularly of polyols such as glycerine and glycols such as hexyleneglycol, polyethyleneglycols and polypropylene glycol. Polyols may be present in a quantity varying from 0.01 to 10% by weight, preferably from 0.05 to 8% by weight relative to the total weight of the composition. According to one preferred embodiment of the invention, the composition comprises at least one polyol, preferably glycerine.

The composition according to the invention may also contain conventional cosmetic adjuvants or additives that will be in one of the two phases depending on their hydrophilic or lipophilic nature, for example such as active cosmetic agents, perfumes, colourants, softeners, buffers, humectants, UV filters (or solar filters), a pH adjuster (for example such as citric acid or sodium hydroxide), and mixtures thereof.

Preferably, the composition according to the invention has a pH of about 4.3+/−0.3. When the composition comprises gluconolactone and/or sodium benzoate, these compounds are effective at low pH. Thus, preferably, a pH of about 4.3+/−0.3 can maintain the efficiency of the preservative, while maintaining skin tolerance.

Among softeners, mention may be made in particular of allantoin, bisabolol, plankton, and some plant extracts such as rose extracts and sweet clover extracts.

The active ingredient(s) that may be present depend on the final purpose of the composition. Among active ingredients that can be used in the composition according to the invention, particularly in the case of a skin care composition, mention may be made for example of enzymes (for example lactoperoxydase, lipase, protease, phospholipase, cellulases); flavonoids such as isoflavones; moisturisers such as protein hydrolysates; sodium hyaluronate; procyanidolic oligomers; vitamins such as vitamin A (retinol), vitamin E (tocopherol), vitamin C (ascorbic acid), vitamin B5 (panthenol), vitamin B3 (niacinamide), derivatives of these vitamins (particularly esters) and mixtures thereof; urea; caffeine; depigmenting agents such as kojic acid, hydroquinone and cafeic acid; salicylic acid and derivatives thereof; alpha-hydroxyacids such as lactic acid and glycolic acid and derivatives thereof; retinoids such as carotenoids and derivatives of vitamin A; hydrocortisone; melatonin; algae extracts (such as extract of blue micro-algae or salicornia extract), extracts of mushrooms, plants, yeast, bacteria; steroids; active anti-bacterial agents such as 2,4,4'-trichloro-2'-hydroxy diphenyl ether (or triclosan), 3,4,4'-trichlorocarbanilide (or triclocarban); tensor agents; ceramides; and essential oils.

UV filters may be present in the composition according to the invention, particularly when it is intended as a solar protection. In particular, these filters may be organic filters and the quantity of active material present may vary from 0.01 to 20% by weight of active material, preferably from 0.1 to 15% by weight, and even better 0.2 to 10% by weight relative to the total weight of the composition.

Among examples of organic filters active in UV-A and/or UV-B that can be added into the composition according to the invention, mention may be made for example of sulfonic function derivatives such as sulfonated derivatives of benzylidene camphor, benzophenone or phenylbenzimidazole, more particularly derivatives of benzylidene camphor, such as benzene 1,4 [di(3-methylidene-camphor 10-sulphonic)] acid (INCI name Terephthalylidene Dicamphor Sulfonic Acid) fabricated under the name "MEXORYL SX" by the CHIMEX company, 4'-sulfo 3-benzylidenecamphor (INCI name Benzylidene Camphor Sulfonic Acid), fabricated under the name "MEXORYL SL" by the CHIMEX company, 2-[4-(camphomethylidene) phenyl], benzimidazole-5-sulfonic acid, phenylbenzimidazole sulfonic acid (INCI name Phenylbenzimidazole Sulfonic Acid), marketed under the name EUSOLEX 232 by the MERCK company; derivatives of para-aminobenzoic acid; salicylic derivatives such as ethyl hexyl salicylate sold under the trade name NEO HELIOPAN OS by Haarmann and Reimer; derivatives of dibenzoylmethane such as Butyl Methoxydibenzoylmethane sold particularly under the trade name PARSOL 1789 by Hoffmann La Roche; cinnamic derivatives such as ethyl-hexyl Methoxycinnamate sold particularly under the trade name PARSOL MCX by Hoffmann La Roche; derivatives of β,β'-diphenylacrylate such as octocrylene (2-ethylhexyl α-cyano-β,β-diphenylacrylate) sold under the trade name UVINUL N539 by the BASF company; derivatives of benzophenone such as Benzophenone-1 sold under the trade name UVINUL 400 by BASF, Benzophenone-2 sold under the trade name UVINUL D50 by BASF, Benzophenone-3 or Oxybenzone, sold under the trade name UVINUL M40 by BASF, Benzophenone-4 sold under the trade name UVINUL MS40 by BASF; derivatives of benzylidene camphor such as 4-Methylbenzylidene camphor sold under the trade name EUSOLEX 6300 by MERCK; derivatives of phenyl benzimidazole such as Benzimidazilate sold under the trade name NEO HELIOPAN AP by Haarmann and Reimer; derivatives of triazine such as Anisotriazine sold under the trade name TINOSORB S by CIBA GEIGY and ethylhexyl triazone sold particularly under the trade name UVINUL T150 by BASF; derivatives of phenyl benzotriazole such as Drometrizole Trisiloxane sold under the trade name SILATRIZOLE by Rhodia Chimie; anthranilic derivatives such as Menthyl anthranilate sold under the trade name NEO HELIOPAN MA by Haarmann and Reimer; derivatives of imidazolines; derivatives of benzalmalonate; and mixtures thereof.

The compositions described above may be conditioned in a known manner, in a flask with a single compartment. The user then needs to shake the flask before pouring the contents onto a cotton pad. It would also be possible to plan that the two phases of the composition are added into two independent compartments in the same flask, with a system being designed to mix them at the time of distribution.

The composition according to the invention may be used for any topical application; in particular, it may form a cosmetic or dermatological composition. In particular, it can be used for care, cleaning and/or make-up removal from the skin, eyes and/or appendages.

Another purpose of this invention is a method for removal of cosmetic make-up, for cleaning and caring of the skin, the eyes and/or appendages, including application of a cosmetic composition as defined above on the skin, eyes and/or appendages.

According to one preferred embodiment of the invention, the composition constitutes an eye make-up removal composition.

Another purpose of this invention is a method of preparing a composition like that defined above, including the following steps:
  a) mix an inulin derivative, a lysophospholipid, a poloxamer, a polypropylene glycol buteth and a derivative of hydrogenated castor oil with water, and optionally a preservative, in order to obtain an aqueous phase;
  b) obtain the oily phase, particularly with at least one oil, that can be a mineral, vegetable or synthetic oil;
  c) introduction of the oily phase obtained in b) into the aqueous phase obtained in a) to obtain the emulsion.

Another example of the method according to the invention could include two steps directly.

The example given below of compositions according to the invention is given for illustrative means and is not at all limitative. Quantities in the example are given as a % by weight, unless mentioned otherwise.

EXAMPLE 1

Choice of the Emulsifying System a) The following raw materials are used in the following examples:
  inulin lauryl carbamate (mixed with glycerine): Inutec SL1®;
  mixture of PPG-26-buteth-26 and PEG-40 hydrogenated castor oil: Solubilisant LRI®;
  poloxamer 184: Synperonic® PE L64;
  glycerine (and) glycine soybean seed extract: Lysofix Liquid®;
  coconut alkanes (and) coco-caprylate/caprate: Vegelight 1214LC®;
  triglycerides of caprylic/capric acids: Miglyol 812N.

The following formulations 1 to 7 are prepared, and the foam obtained after shaking is evaluated. Formulations 5 and 6 comprise 3 of the emulsifiers according to the invention, while formulations 1 to 4 and 7 are comparative.

| Test No. | Oily phase | Aqueous phase | Comments |
|---|---|---|---|
| 1 | Caprylic/capric triglycerides: 10% Vegelight 1214LC: 20% | Lysofix: 3.5% Inutec SL1: 3% Tegobetaine: 0% | aerated foam that collapses more quickly unstable at 2 months |

| Test No. | Oily phase | Aqueous phase | Comments |
|---|---|---|---|
| 2 | | Lysofix: 3.5% Inutec SL1: 0% Tegobetaine: 3% | foams only slightly and forms large bubbles unstable at 15 days |
| 3 | | Lysofix: 3.5% Inutec SL1: 1% Aminol LS 30 (sodium lauroyl sarcosinate): 2% | aerated foam that collapses more quickly unstable at 3 weeks |
| 4 | | Lysofix: 3.5% Inutec SL1: 1% Appygreen 812 (decyl glucoside (and) xylose (and) decyl alcohol (and) water): 1% | foams slightly and forms medium-sized bubbles unstable at 3 months |
| 5 | | Lysofix: 3.5% Inutec SL1: 1% Synperonic PE L64: 0.7% | foams very slightly |
| 6 | | Lysofix: 3.5% Inutec SL1: 1% Synperonic PE L64: 0.5% | foams very slightly |
| 7 | | Lysofix: 3.5% Inutec SL1: 1% Plantacare 200UP (decyl glucoside): 1.5% | aerated foam that collapses more quickly unstable at 2 months |

The results show that the combination of the derivative of inulin (Inutec SL1®), lysophospholipid (Lysofix Liquid®) and poloxamer (Synperonic) foams very slightly, unlike other combinations.

b) Stability of the formulation:

Formulations 8 to 17 in the following table were prepared. The initial formulation is formula 5 in the above table. Only formulation 13 complies with the invention.

| Ingredient | Initial formulation (called "fle") | 8 | 9 | 10 | 11 | 12 | 13* | 14 | 15 | 16 | 17 |
|---|---|---|---|---|---|---|---|---|---|---|---|
| water | Qs | | | | | | | | | | |
| sodium Rectapure | 0.7 | | | | | | | | | | |
| potassium sorbate | 0.5 | | | | | | | | | | |
| CAPRYLIC/CAPRIC TRIGLYCERIDE (Mygliol 812N) | 10 | | | | | | | | | | |
| HYDROGENATED COCONUT ACID & COCOCAPRYLATE/CAPRATE (Vegelight 1214LC ®) | 20 | | | | | | | | | | |
| GLYCERINE & INULIN LAURYL CARBAMATE (Inutech SL1) | 1 | | | | | | | | | | |
| GLYCERINE & *GLYCINE SOJA* (SOYBEAN) SEED EXTRACT (Lysofix Liquid) | 3.5 | | | | | | | | | | |
| POLOXAMER 184 (Synperonic PE L64) | 0.7 | | | | | | | | | | |
| SORBITAN SESQUIOLEATE (SPAN 83) | | 0.15 | | | | | | | | | |
| SORBITAN ISOSTEARATE & POLYGLYCERYL-3 POLYCASTOROLEATE (ARLACEL 1690) | | | 0.15 | | | | | | | | |
| PEG-10 dimethicone (DC ES 5612) | | | | 0.15 | | | | | | | |
| Polysorbate 81 (TWEEN 81) | | | | | 0.15 | | | | | | |
| POLYGLYCERYL 10 LAURATE (DERMOFEEL G10L) | | | | | | 0.15 | | | | | |
| PPG-26-BUTETH-26 & 40% PEG 40 HYDROGENATED CASTOR OIL (Solubilisant LRI) | | | | | | | 0.15 | | | | |
| Dimethicone (and) PEG/PPG-18/18 Dimethicone (DC ES-5226) | | | | | | | | 0.15 | | | |
| CETYL PEG/PPG-10/1 DIMETHICONE & PENTAERYTHRITYL TETRA-DI-T-BUTYL HYDROXYHYDROCINNAMATE (ABIL EM 180) | | | | | | | | | 0.15 | | |
| PEG-8 CAPRYLIC/CAPRIC GLYCERIDES (L.A.S) | | | | | | | | | | 0.15 | 0.35 |

The following comments were made:

For the initial formulation, immediately after shaking, a transparent bottom and a surface emulsion are observed with slight foaming At D+1, the aqueous phase is transparent but the surface has an oily exudate appearance.

The following table contains comments on the other formulations:

| | Formulation | | | | | | | | | |
|---|---|---|---|---|---|---|---|---|---|---|
| | 8 | 9 | 10 | 11 | 12 | 13* | 14 | 15 | 16 | 17 |
| Immediate observation after shaking | slight foaming less than fle | slight foaming less than fle | considerable foaming | very slight foaming aqueous phase at the bottom but white with emulsion on the surface | fairly considerable foaming more than fle | slight foaming equivalent to fle | foam equivalent to fle | more foaming than fle | slight foaming less than fle | slight foaming but limited area |
| Foam classification | 2 | 4 | 10 | 1 | 9 | 7 | 8 | 6 | 3 | |
| Observation d + 1 | cloudy aqueous phase at bottom limited exudatiom area | cloudy aqueous phase at bottom limited exudatiom area | non-homogeneous interface slightly cloudy aqueous phase and upper interface oily exudation limit | separated emulsion oily phase separation | slight presence of foam always present therefore visually impossible to see oily phase separation slightly cloudy aqueous phase | slightly cloudy aqueous phase surface with presence of a few bubbles | transparent aqueous phase but non-homogeneous water-emulsion interface presence of bubbles | transparent aqueous phase at bottom a few bubbles on the surface but no phase separation | transparent aqueous phase slight exudation on surface | |
| Quality classification at D + 1 | 2 | 5 | 8 | 9 | 4 | 1 | 7 | 6 | 3 | |

Formulation 13 (13*) is the only formulation according to the invention, the others are comparative.

The results thus show that formulation 13, that comprises a polypropylene glycol buteth and a derivative of hydrogenated castor oil, and that is a formulation according to the invention, has little foam and an aqueous phase with an attractive appearance. This is the only tested formulation that does not have much foam and that is stable.

EXAMPLE 2

Stability of Compositions Obtained

The stability of the following compositions 18 to 28 is evaluated.

| | | Aqueous phase | | | |
|---|---|---|---|---|---|
| Test No. | Oily phase | TA system | Preservatives | Stability | Comments |
| 18 | Caprylic/Capric Triglycerides: 10% Vegelight 1214 LC 20: % KM-72S 1% | Lysofix 3.5% Synperonic PE L64 0.7% Solubilisant LRI 1% | K Sorbate 0.5% | 3 months: KO | Stability not conforming |
| 19 | Caprylic/Capric Triglycerides 10% Isohexadecane 20% KM-72S 1% | Lysofix 3.5% Synperonic PE L64 0.7% Solubilisant LRI 1% | K Sorbate 0.5% | 2 months: KO at 40° C. and 45° C. | Stability not conforming |
| 20 | Caprylic/Capric Triglycerides 10% Vegelight 1214 LC 20% KM-72S 1% | Lysofix 3.5% Synperonic PE L64 0.7% Solubilisant LRI 1% | Pentylene Glycol 2.25% Caprylyl Glycol 0.5% | 1 month: emulsion phase KO at 40° C. and 45° C. | KO |

-continued

| Test No. | Oily phase | Aqueous phase TA system | Preservatives | Stability | Comments |
|---|---|---|---|---|---|
| 21 | Caprylic/Capric Triglycerides 10% Vegelight 1214 LC 20% KM-72S 1% | Lysofix 3.5% Synperonic PE L64 0.7% Solubilisant LRI 1% | Methylparaben 0.2% Phenoxyethanol 0.5% | 1 month: Stable limit emulsion Float at all temperatures | Limit |
| 22 | Caprylic/Capric Triglycerides 10% Vegelight 1214 LC 20% KM-72S 1% | Lysofix 3.5% Synperonic PE L64 0.7% Solubilisant LRI 1% | propanediol & phenethyl alcohol & undecyl alcohol & tocopherol (Sensiva PA-30) 2% | 1 month: stable limit emulsion Float at all temperatures | Limit |
| 23 | Caprylic/Capric Triglycerides 10% Vegelight 1214 LC 20% KM-72S 1% | Lysofix 3.5% Synperonic PE L64 0.7% Solubilisant LRI 1% | propanediol & phenethyl alcohol & undecyl alcohol & tocopherol (Sensiva PA-40) 2% | emulsion phase KO at D + 15 | KO |
| 24 | Caprylic/Capric Triglycerides 10% Vegelight 1214 LC 20% KM-72S 1% | Lysofix 3.5% Synperonic PE L64 0.7% Solubilisant LRI 1% | Caprylyl Glycol (and) Glyceryl Caprylate (and) Glycerine (and) Phenylpropanol (Dermosoft LP) 4% | 4 phases at D + 1 | KO |
| 25 | Caprylic/Capric Triglycerides 10% Vegelight 1214 LC 20% KM-72S 1% | Lysofix 3.5% Synperonic PE L64 0.7% Solubilisant LRI 1% | Methylparaben 0.25% Propylparaben 0.1% | 1 month: OK 3 months: KO | Stability not conforming Recrystallisation of parabens |
| 26 | Caprylic/Capric Triglycerides 10% Vegelight 1214 LC 20% KM-72S 1% | Lysofix 3.5% Synperonic PE L64 0.7% Solubilisant LRI 1% | Methylparaben 0.25% + 1% Glycerin Propylparaben 0.1% | 3 months: KO | Stability not conforming Recrystallisation of parabens |
| 27 | Caprylic/Capric Triglycerides 10% Vegelight 1214 LC 10% Isohexadecane 10% KM-72S 1% | Lysofix 3.5% Synperonic PE L64 0.7% Solubilisant LRI 1% | Methylparaben 0.25% + 1% Glycerin Propylparaben 0.1% | 3 months: KO at 45° | Stability not conforming |
| 28 | Caprylic/Capric Triglycerides 10% Vegelight 1214 LC 10% Isohexadecane 10% KM-72S 1% | Lysofix 3.5% Synperonic PE L64 0.7% Solubilisant LRI 1% (with or without Inutec SL1 1%) | gluconolactone & sodium benzoate & calcium gluconate (Geogard Ultra) 2% | 3 months OK | Stability conforming |

KO = not stable

The results thus show that the composition comprising the surfactant system and a preservative according to the invention is stable.

EXAMPLE 3

Composition

A composition according to the invention is prepared with the following ingredients (percentages are by weight of the total composition):
water qsp
0.7% NaCl
7.2% glycerine
2% GLUCONOLACTONE & SODIUM BENZOATE & CALCIUM GLUCONATE (GEOGARD ULTRA)
9.8% caprylic/capric triglyceride (Mygliol 812N)
10% hydrogenated coconut acid & coco-caprylate/caprate (VEGELIGHT 1214 LC)
9.98% isohexadecane (Creasil IHGC)
0.1% simethicone (XIAMETER ACP-1500)
1% inulin lauryl carbamate & glycerine (INUTEC SL1)
3.5% glycerine & glycine soybean seed extract (LYSO-FIX LIQUID)
0.7% poloxamer 184 (SYNPERONIC PE L64)
1% PPG-26-buteth-26 & PEG 40 hydrogenated castor oil (SOLUBILISANT LRI)

The invention claimed is:

1. Cosmetic composition composed of an aqueous phase and a separate water-in-oil or oil-in-water phase, the composition comprising an emulsifying system containing an inulin derivative, a lysophospholipid, a poloxamer, a polypropylene glycol buteth and a derivative of hydrogenated castor oil, and said water-in-oil or oil-in-water emulsion comprising at least 20% by weight of an oil phase in relation to the total weight of the composition.

2. Composition according to claim 1, also comprising gluconolactone and/or sodium benzoate.

3. Composition according to claim 1, wherein the global aqueous phase:oily phase ratio is between 40:60 and 80:20.

4. Composition according to claim 1, wherein the oily phase is present with a content of between 20% and 40% by weight of the total weight of the composition.

5. Composition according to claim 1, wherein the emulsifying system is present with a content of between 2% and 10% by weight of the total weight of the composition.

6. Composition according to claim 1, wherein the derivative of inulin is an inulin carbamoyl with an alkyl isocyanate.

7. Composition according to claim 6, wherein the derivative of inulin is an inulin carbamoyl with lauryl isocyanate.

8. The composition of claim 7, wherein said derivative is inulin lauryl carbamate.

9. Composition according to claim 1, wherein the polypropylene glycol buteth satisfies the following formula (II):

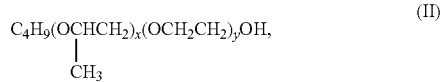

(II)

in which x and y are integers that may be identical or different, between 1 and 50.

10. The composition of claim 9, wherein x and y are integers that may be identical or different, between 10 and 35.

11. Composition according to claim 1, wherein the polypropylene glycol buteth is chosen from among PPG-12-buteth-16, PPG-9-buteth-12, PPG-26-buteth-26 and PPG-28-buteth-35, and/or wherein the derivative of hydrogenated castor oil is an oxyethylenated hydrogenated castor oil.

12. Composition according to claim 1, wherein the poloxamer satisfies the following formula (III):

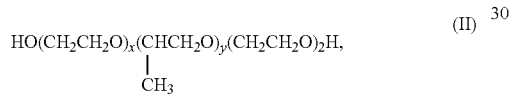

(II)

in which x and y are integers that may be identical or different, between 1 and 50.

13. Composition according to claim 1, wherein the lysophospholipid is lysophosphatidylcholin, that has following formula:

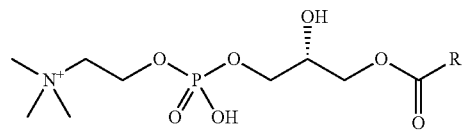

in which R is a fatty acid chain, in particular comprising 10 to 25 carbon atoms.

14. Composition according to claim 1, wherein the oily phase comprises at least one oil chosen from among mineral oils, vegetable oils and synthetic oils.

15. Composition according to claim 1, further comprising at least one antifoaming agent.

16. Composition according to claim 1, wherein the compositino has a pH of about 4.3 +/− 0.3.

17. Composition according to claim 1, wherein the oily phase is present with a content of between 25% and 35% by weight of the total weight of the composition.

18. Composition according to claim 1, wherein the emulsifying system is present with a content of between 3% and 7% by weight of the total weight of the composition.

19. Method of preparing a composition according to claim 1, including the following steps:
   a) mix an inulin derivative, a lysophospholipid, a poloxamer, a polypropylene glycol buteth and a derivative of hydrogenated castor oil with water, in order to obtain an aqueous phase;
   b) obtain the oily phase, particularly with at least one oil, that can be a mineral, vegetable or synthetic oil;
   c) introduction of the oily phase obtained in b) into the aqueous phase obtained in a) to obtain the emulsion.

20. Cosmetic method of make-up removal, cleaning and/or care of the skin, eyes and/or appendages, wherein a cosmetic composition according to claim 1 is applied on the skin, eyes and/or appendages.

* * * * *